US006400875B1

(12) United States Patent
Lincoln et al.

(10) Patent No.: US 6,400,875 B1
(45) Date of Patent: Jun. 4, 2002

(54) METHOD FOR PROTECTING A FIBER OPTIC PROBE AND THE RESULTING FIBER OPTIC PROBE

(75) Inventors: Danny Lincoln, Commerce; Tim Harrell, Norcross; David Farquhar, Commerce; Joe Papp; Krishna Kumar, both of Duluth, all of GA (US)

(73) Assignee: Spectrx, Inc., Norcross, GA (US)

( * ) Notice: Subject to any disclaimer, the term of this patent is extended or adjusted under 35 U.S.C. 154(b) by 0 days.

(21) Appl. No.: 09/431,180

(22) Filed: Nov. 1, 1999

Related U.S. Application Data
(60) Provisional application No. 60/106,749, filed on Nov. 2, 1998.

(51) Int. Cl.[7] .................................................. G02B 6/04
(52) U.S. Cl. .................... 385/115; 385/116; 385/119; 385/120; 606/15
(58) Field of Search ........................ 385/115–120, 123, 385/139; 606/15, 16

(56) References Cited

U.S. PATENT DOCUMENTS

| | | | |
|---|---|---|---|
| 5,166,756 A | * | 11/1992 | McGee et al. ............... 356/446 |
| 5,196,005 A | * | 3/1993 | Doiron et al. ................ 606/7 |
| 5,208,890 A | * | 5/1993 | Kohler et al. ............... 385/115 |
| 5,351,332 A | * | 9/1994 | Cook ........................ 385/116 |
| 5,402,508 A | * | 3/1995 | O'Rourke et al. ............ 385/31 |
| 5,489,536 A | | 2/1996 | Ekechukwu |
| 5,901,261 A | | 5/1999 | Wach |
| 5,953,477 A | | 9/1999 | Wach et al. |
| 6,201,915 B1 | * | 3/2001 | Rizkin et al. ............... 385/115 |

* cited by examiner

Primary Examiner—Hemang Sanghavi
(74) Attorney, Agent, or Firm—Fleshner & Kim, LLP

(57) ABSTRACT

A fiber optic probe is provided that includes a housing, at least one optical fiber disposed within the housing, one end of each of the at least one optical fiber being disposed adjacent an opening in the housing forming a probe face, a binding agent that binds the at least one optical fiber within the housing, and a protective coating sealingly covering the probe face to prevent contaminants from contacting the at least optical fiber. A method for protecting a fiber optic probe having a housing, at least one optical fiber disposed within the housing, one end of each of the at least one optical fiber being disposed adjacent an opening in the housing forming a probe face, and a binding agent that binds the at least one optical fiber within the housing, includes polishing the probe face to create a substantially flat probe face, cleaning the probe face after polishing the probe face and sealing the probe face with a protective coating.

15 Claims, 5 Drawing Sheets

METHOD FOR PROTECTING A FIBER OPTIC PROBE AND THE RESULTING FIBER OPTIC PROBE

This application claim benefit of provisional No. 60/106,749 filed Nov. 2, 1998.

BACKGROUND OF THE INVENTION

1. Field of the Invention

The invention is directed to method of protecting a fiber optic probe and the resulting fiber optic probe.

2. Background of the Related Art

Optical fibers and collections or bundles of such optical fibers are now commonly used for illumination, remote viewing and remote spectroscopy in, for example, medicine, industry and science. The function of a particular optical fiber in a bundle can be illumination of a subject or collection of light from a subject or sample for remote viewing or spectroscopic analysis of the light returned. It is common practice to use a binding agent, adhesive or epoxy material to hold the optical fibers together and in place within a probe housing. Once fixed in place, it is common practice to polish the ends of the optical fibers, and therefore the binding agent and the housing, to a common surface level.

For example, FIG. 1 shows an exemplary endoscope 1 employing a fiber optic probe 10. The endoscope 1 includes a transmit optical fiber bundle 20a, which conveys excitation electromagnetic radiation from a radiation source 2 to a target tissue. The endoscope 1 further includes a return optical fiber bundle 20b for communicating reflected/scattered electromagnetic radiation or fluorescent emissions from a target tissue to a detector 3. The transmit and return optical fibers can be co-located; or can be the same optical fibers. The endoscope may further include a handle 4 for positioning the fiber optic probe 10.

FIG. 1B shows the structure of fiber optic probe 10 of the endoscope 1. The apparatus includes a housing 60 having a long body portion 5, which is intended to be inserted into a body of a patient. The body portion 5 may have a diameter that is sufficiently small so that the body portion 5 can be inserted into blood vessels, or a natural lumen or body cavity of a patient.

As shown in FIG. 2, each optical fiber contains a core 20a, preferably formed of glass or plastic, and a cladding 20b, preferably formed of doped glass or plastic. The optical fibers 20 may also include a buffer 20c and/or a jacket 20d, preferably formed of protective materials, such as, for example, plastic or polyimide. As shown in FIGS. 1B, 1C and 2, the optical fibers 20 are bundled using a binding agent 30.

A microscopic examination of a fiber optic probe that has been constructed and polished as discussed above, frequently reveals that the binding agent and optical fiber components are not at the same height. Either the materials are polished back further due to their softer nature, or the materials shrink back upon aging. As shown in FIG. 2, which shows the face 15 of the fiber optic probe 10 of FIG. 1, this creates spaces 35 between the ends or faces of the optical fibers 36 and the binding agent 30 where contaminants 40, such as bits of dust, polishing compound, adhesive residue and the like can collect. When the ends of such optical fibers 26 are wiped for cleaning, the materials collected in these spaces may be moved to the ends or faces of the optical fibers 36 and leave the fiber faces 36 with more dirt and residue than before cleaning.

In addition, there are materials in medicine and industry which one would like to minimize collecting on the probe in the void spaces or on the surfaces of the fibers.

SUMMARY OF THE INVENTION

An object of the invention is to solve at least the above problems and/or disadvantages and to provide at least the advantages described hereinafter.

According to a preferred embodiment of the invention, a fiber optic probe comprises a housing, at least one optical fiber disposed within the housing, one end of each of the at least one optical fiber being disposed adjacent an opening in the housing forming a probe face, a binding agent that binds the at least one optical fiber within the housing, and a protective coating sealingly covering the probe face to prevent contaminants from contacting the at least one optical fiber. The at least one optical fiber may comprise a plurality of optical fibers, and the protective coating may sealingly cover portions of the binding agent located between the plurality of optical fibers.

The protective coating is preferably formed of an adhesive, an epoxy or a polymer. The binding agent is also preferably formed of an adhesive, an epoxy and a polymer. The protective coating is preferably polished so that a cone angle of the at least one optical fiber is preserved, or is substantially the same as a cone angle that the at least one optical fiber has without the protective coating.

The at least one optical fiber may receive light from a greater subject surface area with the protective coating than without the protective coating. Further, the at least one optical fiber may illuminate a greater subject surface area with the protective coating than without the protective coating.

Further, a preferred method embodying the invention for protecting a fiber optic probe that includes a housing, at least one optical fiber disposed within the housing, one end of the optical fiber being disposed adjacent an opening in the housing forming a probe face, and a binding agent that binds the at least one optical fiber within the housing, comprises polishing the probe face, cleaning the probe face after polishing the probe face, and sealing the probe face with a protective coating. The method may further comprise polishing the protective coating. The step of polishing the protective coating may comprise polishing the protective coating to control the spot size of the at least one optical fiber. The step of cleaning the probe face may comprise ultrasonic cleaning, or flooding the probe head with at least one of water and solvent at normal or high pressure.

The protective coating is preferably formed of an adhesive, an epoxy and/or a polymer. The protective coating is preferably polished so that a cone angle of the at least one optical fiber is preserved. Further, the protective coating may be configured so that the at least one optical fiber receives light from a greater subject surface area with the protective coating than without the protective coating. Furthermore, the protective coating may be configured so that the at least one optical fiber illuminates a greater subject surface area with the protective coating than without the protective coating.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings, in which like reference numerals refer to like elements, and wherein.

DETAILED DESCRIPTION OF PREFERRED EMBODIMENTS

Figure 1A:
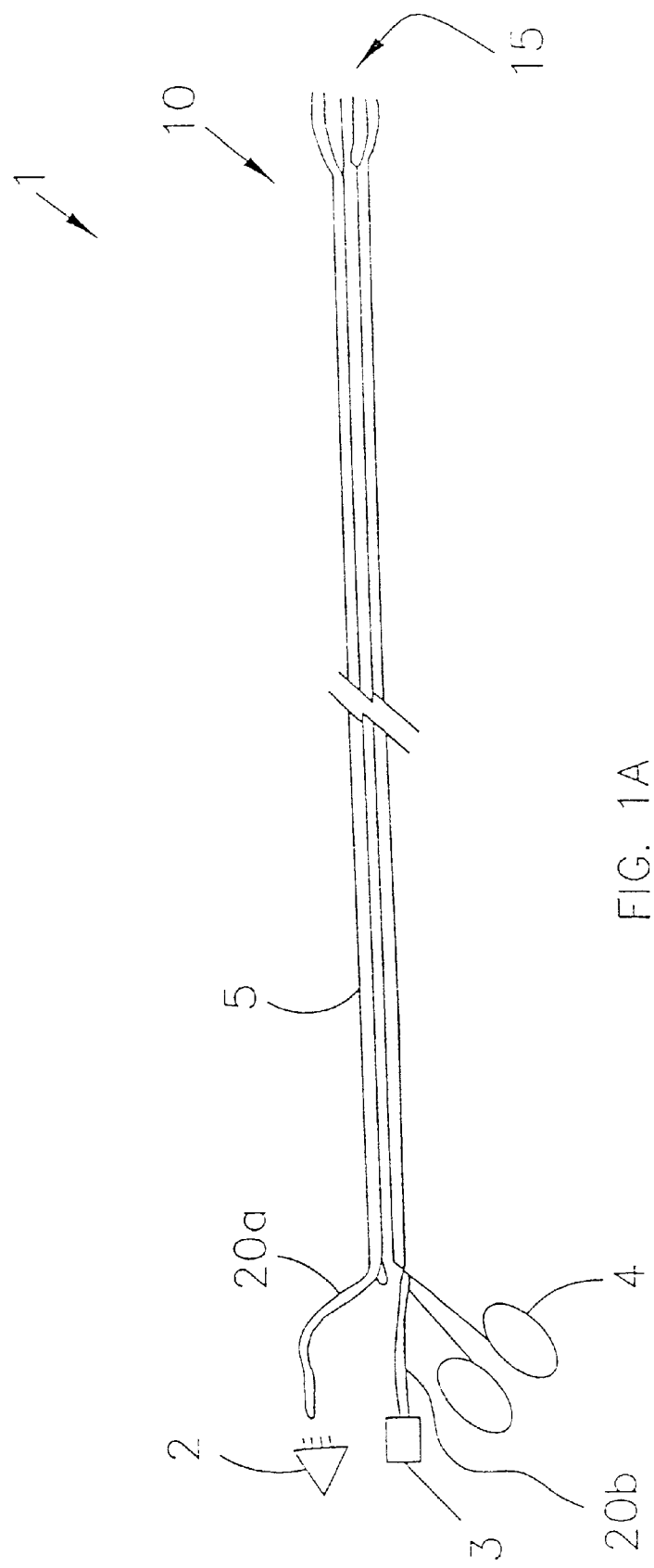
FIGS. 1A–1C show an exemplary endoscope employing a fiber optic probe.
Figure 1B:
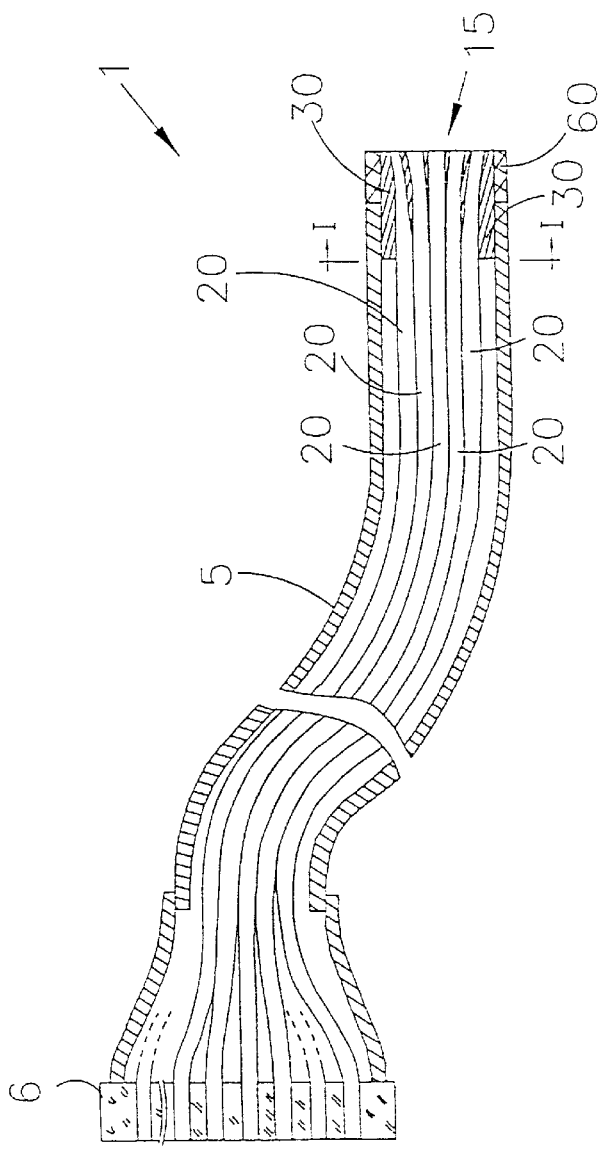
Figure 1C:
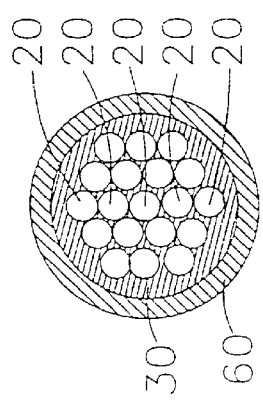
Figure 2:
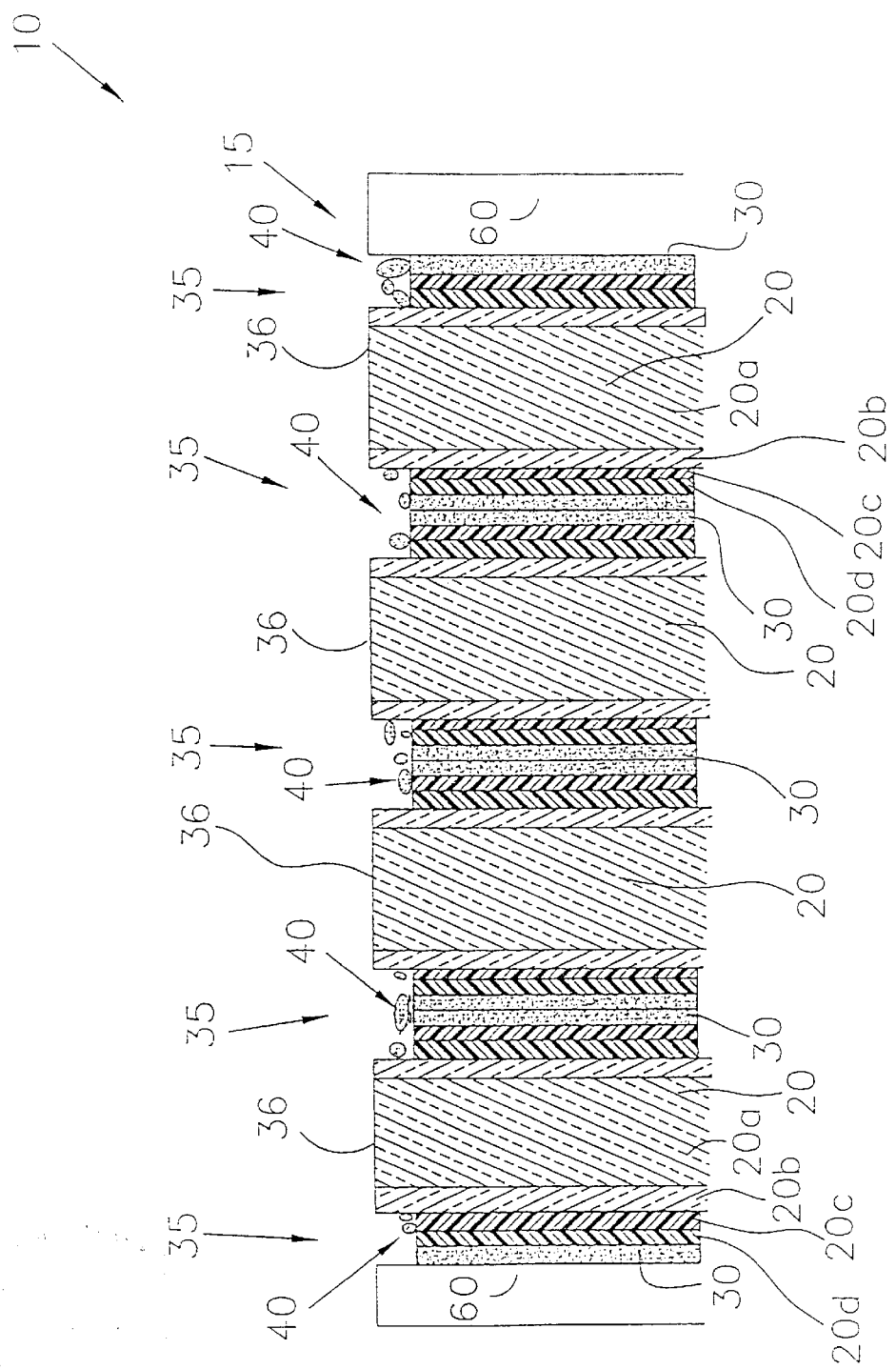
FIG. 2 shows a face of a related art fiber optic probe littered with contaminants.
Figure 3:
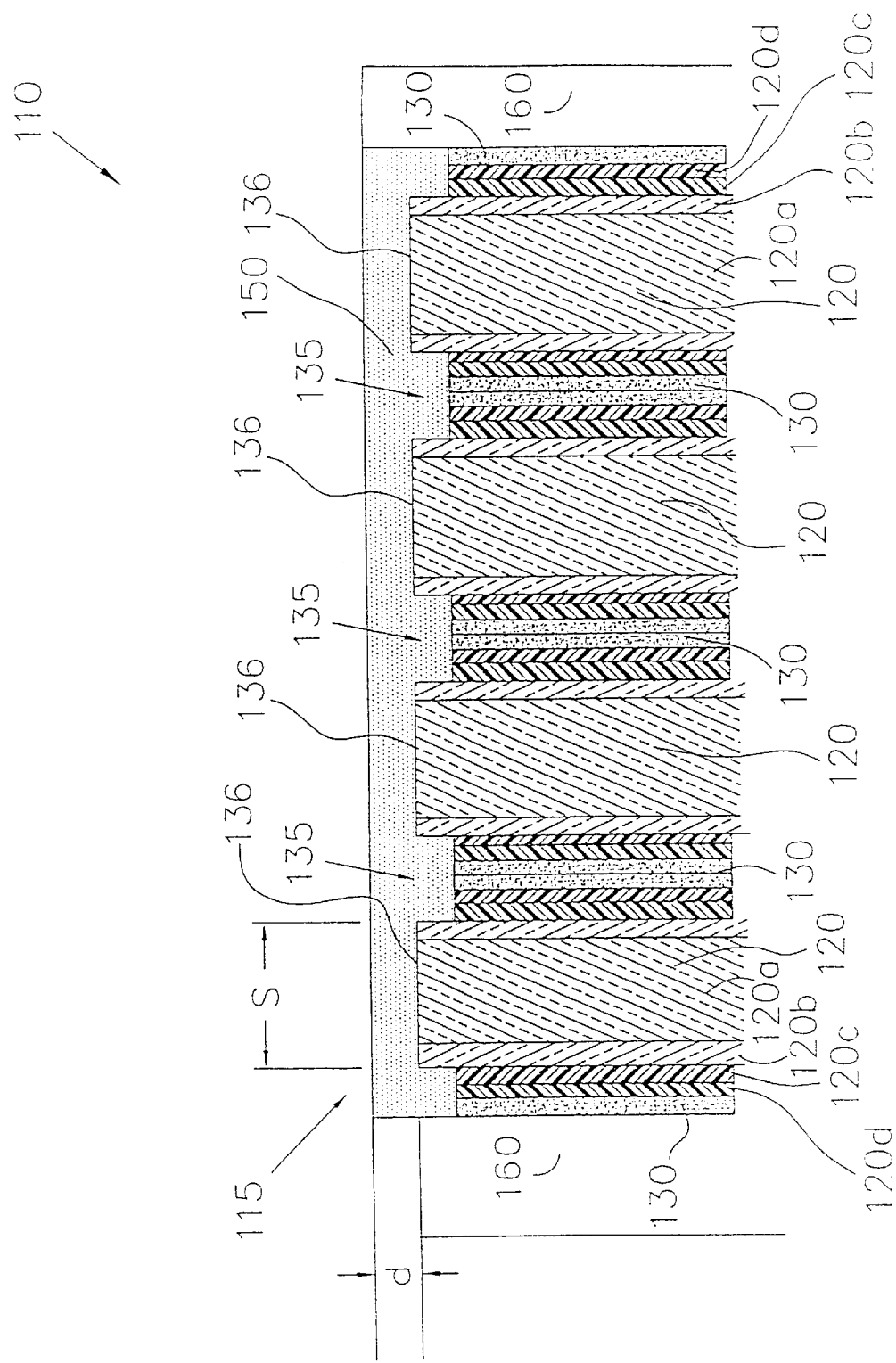
FIG. 3 shows a face of a fiber optic probe according to a preferred embodiment of the invention.

FIG. 3 shows a face 115 of a fiber optic probe 110 according to a preferred embodiment of the invention. The fiber optic probe 110 includes a housing 160 in which optical fibers 120 are bundled using a binding agent 130. Each optical fiber 120 contains a core 120a, preferably formed of glass or plastic, and a cladding 120b, preferably formed of doped glass or plastic. The optical fibers 120 may also include a buffer 120c and/or a jacket 120d, preferably formed of protective materials, such as, for example, plastic or polyimide. The binding agent 130 is preferably formed of an adhesive, an epoxy and/or a polymer; however, other materials may also be appropriate.

Spaces 135 are formed between the ends or faces of the optical fibers 136 and the binding agent 130 and/or the buffer 120c and jacket 120d of the optical fiber 120 when the face of the probe 115 is polished after manufacture. A protective coating 150 is bonded to the probe face so that it covers and substantially fills the spaces 135, as well as covers the ends or faces of the optical fibers 136. The protective coating 150 is preferably formed of an adhesive, an epoxy or a polymer; however, other materials may also be appropriate. The protective coating 150 prevents contaminants, such as, for example, bits of dust, polishing compound, adhesive residue and the like from collecting on the ends or faces of the optical fibers 136 and in the spaces 135.

According to a preferred method of the invention, after manufacture of a fiber optic probe, the face of the fiber optic probe is polished. After polishing, the ends or faces of the optical fibers 136 may be substantially flush with the binding agent 130, or spaces 135 may be formed between the ends or faces of the optical fibers 136 and the binding agent 130. The probe face 115 is then cleaned either by ultrasonic cleaning, which employs sounds waves to dislodge and remove contaminants from the spaces 135, or by flooding the probe face 115 with, for example, water or a solvent at, for example, normal or high pressure to dislodge and remove the contaminants from the spaces 135. The probe face 115 is then sealed with a protective coating 150.

The protective coating is polished to obtain desired optical properties. That is, the "cone angle," or the maximum angle of which the optical fiber will support light coming or going into the optical fiber, of the respective optical fibers 120 is preserved, while the "spot size," or surface area of a subject which the optical fiber illuminates or from which the optical fiber receives reflected light, of the respective optical fibers 120 is increased.

Figure 4:
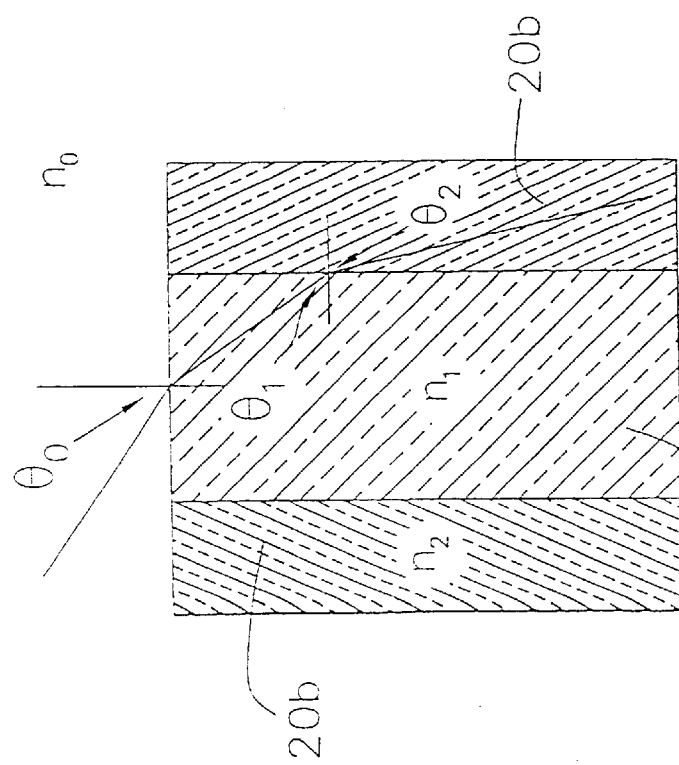
FIG. 4 is a schematic diagram of light entering a fiber optic probe without the protective coating of the invention.

For example, referring to FIG. 4, for a fiber optic probe without a protective coating, Snell's Law applies as follows:

$$n_1 \sin \theta_1 = n_2 \sin \theta_2$$

where $n_1$ is the index of refraction of the optical fiber, $n_2$ is the index of refraction of the fiber cladding, $\theta_1$ is the angle of incidence and $\theta_2$ is the angle of refraction. For the critical angle calculation, $\theta_1$ is set equal to $\theta_{Critical}$ where $\theta_2$ equals $\pi/2$, then $$n_1 \sin \theta_{Critical} = n_2 \sin (\pi/2) = n_2$$

so that $$\sin \theta_{Critical} = n_2/n_1$$

which is usually defined as the numeric aperture (NA) of the optical fiber. To calculate the "cone angle," Snell's Law for the critical angle case is applied where $$n_0 \sin \theta_{max} = n_1 \sin (\pi/2 - \theta_{Critical}) = n_1 \cos \theta_{Critical} = n_1 \sqrt{1 - \sin^2 \theta_{Critical}}$$

so that $$n_0 \sin \theta_{max} = \sqrt{n_1^2 - n_2^2}$$

Figure 5:
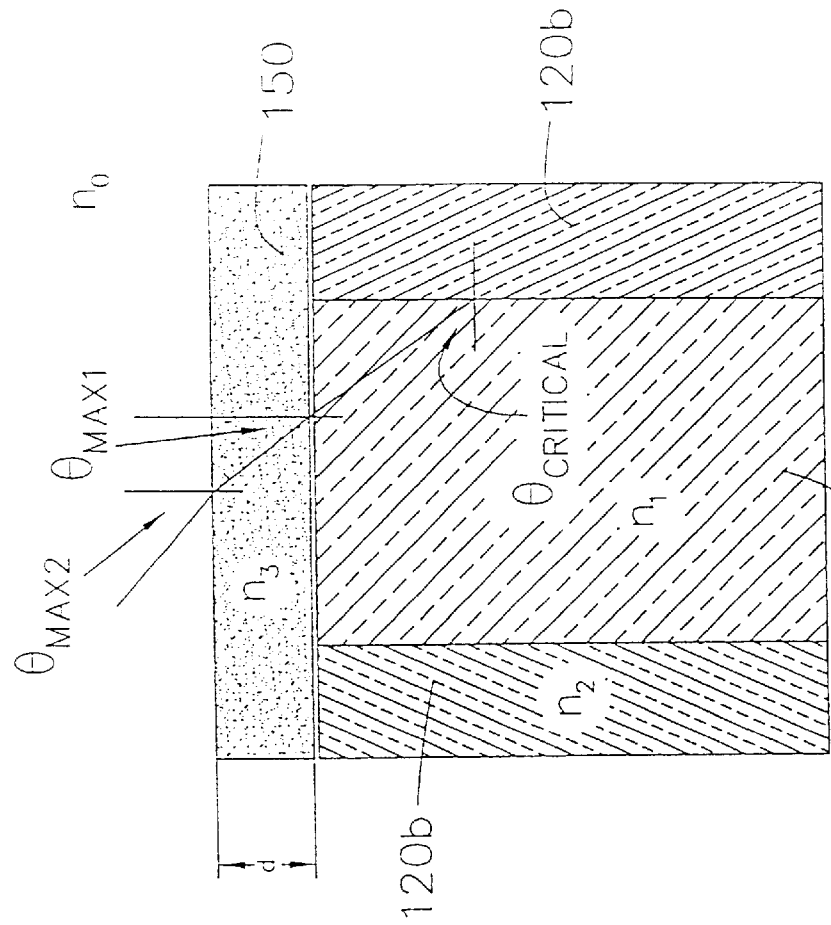
FIG. 5 is a schematic diagram of light entering a fiber optic probe according to a preferred embodiment of the invention.

As shown in FIG. 5, with a protective coating having an index of refraction $n_3$ the following applies:

$$n_0 \sin \theta_{max2} = n_3 \sin \theta_{max} = \sqrt{n_1^2 - n_2^2}$$

so that the resulting cone angle, $\theta_{max2}$, is the same after the protective coating as if the protective coating were not present, but the effective spot size at the surface of the layer is $d \tan \theta_{max1}$, which is larger in radius than the fiber core radius, where d is the thickness of the protective coating 150 between a surface of the protective coating 150 located adjacent the face of the optical fiber 136 and the outer surface of the protective coating 150.

Depending on the tissue being interrogated, the material (and thus, the index of refraction) and thickness of the protective coating may be selected so as to obtain the desired parameters while minimizing cross-talk between the various optical fibers. Further, the material of the protective coating may be selected so that the fiber optic probe may be disinfected and/or sterilized without affecting the optical characteristics of the protective coating.

Such a protective coating on the probe face makes cleaning and maintenance of the fiber optic probe easier. By using high refractive index material, one can also focus each optical fiber to a tighter spot by effectively decreasing the numeric aperture (NA) of the optical fiber. By polishing the protective coating to a specific thickness, one can tailor the spot size of each optical fiber at the probe face.

The foregoing embodiments and advantages are merely exemplary and are not to be construed as limiting the present invention. The present teaching can be readily applied to other types of apparatuses. The description of the invention is intended to be illustrative, and not to limit the scope of the claims. Many alternatives, modifications, and variations will be apparent to those skilled in the art. In the claims, means-plusfunction clauses are intended to cover the structures described herein as performing the recited function and not only structural equivalents but also equivalent structures.

What is claimed is:

1. A fiber optic probe comprising:

a housing;

at least one optical fiber disposed within the housing, one end of each of the at least one optical fiber being disposed adjacent an opening in the housing forming a probe face;

a binding agent that binds the at least one optical fiber within the housing; and a protective coating sealingly covering the probe face to prevent contaminants from contacting the at least one optical fiber, wherein the protective coating is polished so that a cone angle of the at least one optical fiber is substantially the same as a cone angle that the at least one optical fiber has without the protective coating.

2. The fiber optic probe according to claim 1, wherein the protective coating is formed of a material selected from the group consisting of an adhesive, an epoxy and a polymer.

3. The fiber optic probe according to claim 1, wherein the binding agent is formed of a material selected from the group consisting of an adhesive, an epoxy and a polymer.

4. The fiber optic probe according to claim 1, wherein the at least one optical fiber receives light from a greater subject surface area with the protective coating than without the protective coating.

5. The fiber optic probe according to claim 1, wherein the at least one optical fiber illuminates a greater subject surface area with the protective coating than without the protective coating.

6. The fiber optic probe according to claim 1, wherein the at least one optical fiber comprises a plurality of optical fibers, and wherein the protective coating also sealingly covers portions of the binding agent located between the plurality of optical fibers.

7. A method for protecting a fiber optic probe, the fiber optic probe comprising a housing, at least one optical fiber disposed within the housing, one end of each of the at least one optical fiber being disposed adjacent an opening in the housing forming a probe face, and a binding agent that binds the at least one optical fiber within the housing, the method comprising:

polishing the probe face;

cleaning the probe face after polishing the probe face;

sealing the probe face with a protective coating; and polishing the protective coating, wherein the step of polishing the protective coating comprises polishing the protective coating so that a cone angle of the at least one optical fiber is substantially the same as a cone angle that the at least one optical fiber has without the protective coating.

8. The method according to claim 7, where step of polishing the protective coating comprises polishing the protective coating to control a spot size of the at least one optical fiber.

9. The method according to claim 7, wherein the step of cleaning the probe face comprises ultrasonic cleaning.

10. The method according to claim 7, wherein the step of cleaning the probe face comprises flooding the probe head with at least one of water and solvent.

11. The method according to claim 7, wherein the protective coating is formed of a material selected from the group consisting of an adhesive, an epoxy and a polymer.

12. The method according to claim 7, wherein the sealing step comprises forming the protective coating so that the at least one optical fiber receives light from a greater subject surface area with the protective coating than without the protective coating.

13. The method according to claim 7, wherein the sealing step comprises forming the protective coating so that the at least one optical fiber illuminates a greater subject surface area with the protective coating than without the protective coating.

14. The method according to claim 7, wherein the at least one optical fiber comprises a plurality of optical fibers, and wherein the sealing step comprises forming the protective coating so that it covers portions of the binding agent between the plurality of optical fibers, and so that the probe face is substantially flat.

15. A method for protecting a fiber optic probe, the fiber optic probe comprising a housing, at least one optical fiber disposed within the housing, one end of each of the at least one optical fiber being disposed adjacent an opening in the housing forming a probe face, and a binding agent that binds the at least one optical fiber within the housing, the method comprising:

polishing the probe face;

cleaning the probe face after polishing the probe face;

sealing the probe face with a protective coating; and polishing the protective coating so that a thickness of the protective coating results in the at least one optical fiber having substantially the same cone angle that the optical fiber would have without the protective coating.

\* \* \* \* \*